US007229450B1

United States Patent
Chitre et al.

(10) Patent No.: US 7,229,450 B1
(45) Date of Patent: Jun. 12, 2007

(54) KINK RESISTANT INTRODUCER WITH MAPPING CAPABILITIES

(75) Inventors: Yougandh Chitre, Valencia, CA (US); Kevin L. Morgan, Simi Valley, CA (US); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 857 days.

(21) Appl. No.: 10/365,270

(22) Filed: Feb. 11, 2003

(51) Int. Cl.
*A61B 5/042* (2006.01)

(52) U.S. Cl. ........................... 606/129; 600/373
(58) Field of Classification Search ............... 604/158, 604/163, 164.01, 164.13, 264, 523; 606/108, 606/129; 600/372–375, 377, 381; 607/115–116, 607/119–132
See application file for complete search history.

(56) References Cited

U.S. PATENT DOCUMENTS

| 3,865,118 A * | 2/1975 | Bures ........................... 607/123 |
| 4,306,562 A | 12/1981 | Osborne ....................... 128/348 |
| 5,409,469 A | 4/1995 | Schaerf ........................ 604/282 |
| 5,713,867 A | 2/1998 | Morris ......................... 604/164 |
| 5,785,706 A | 7/1998 | Bednarek ...................... 606/41 |
| 5,814,027 A | 9/1998 | Hassett et al. ............... 604/286 |
| 5,964,796 A | 10/1999 | Imran .......................... 607/122 |
| 6,002,956 A * | 12/1999 | Schaer ......................... 600/381 |
| 6,478,777 B1 * | 11/2002 | Honeck et al. ........ 604/164.01 |
| 6,755,812 B2 * | 6/2004 | Peterson et al. ............. 604/528 |
| 6,979,319 B2 * | 12/2005 | Manning et al. ....... 604/164.05 |
| 6,988,007 B1 * | 1/2006 | Morgan et al. .............. 607/123 |
| 2003/0083560 A1 * | 5/2003 | Osypka ....................... 600/374 |

FOREIGN PATENT DOCUMENTS

| EP | 0655257 A2 | 5/1995 |
| EP | 0655257 A3 | 5/1996 |
| WO | WO 97/40880 | 11/1997 |

\* cited by examiner

*Primary Examiner*—Carl Layno
*Assistant Examiner*—Kristen Mullen (57) ABSTRACT

An introducer system for use with a pacemaker lead includes a plastic sheath compatible for insertion within a body, a first end configured for insertion into the body with a second end extending out of the body. A central lumen of the sheath is configured to permit introduction of the lead and includes a flexible, kink-resistant section smooth on its outer surface with a helical pleat defining a helical groove enabling a conductor extending from the mapping probe to the pacing system analyzer to be received in the helical groove of the sheath. A mapping probe at the first end of the sheath is connectable to a pacing system analyzer for seeking a location on the myocardial surface of the heart or an endocardial location at which optimal pacing parameters can be achieved prior to implantation of the lead.

15 Claims, 12 Drawing Sheets

KINK RESISTANT INTRODUCER WITH MAPPING CAPABILITIES

FIELD OF THE INVENTION

The present invention relates generally to an introducer system having a kink resistant sheath for the insertion of leads, catheters and other elongated instruments into the body and more particularly to a kink resistant introducer system which has mapping capabilities for optimally positioning a transvenous pacemaker lead or an epicardial pacemaker lead at the myocardial surface of the heart.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. However, the appended claims are not intended to be limited to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing, or for sensing electrical signals produced by the heart, or for both pacing and sensing in which case a single lead serves as a bi-directional pulse transmission link between the pacemaker and the heart or may be used to deliver defibrillation shocks to the patient. A typical transvenous type pacing/sensing lead, that is, a lead which is inserted into a vein and guided therethrough into a cavity of the heart, includes at its distal end an electrode designed to contact the endocardium, the tissue lining the inside of the heart. The lead further includes a proximal end having a connector terminal pin adapted to be received by a mating socket in the pacemaker. A flexible, coiled or cabled conductor surrounded by an insulating tube or sheath typically couples the connector terminal pin at the proximal end and the electrode at the distal end.

The implantable cardiac stimulation leads with which the present invention is concerned may take the form of pacemaker leads capable of pacing and sensing in at least one chamber of the heart. Indeed, the present invention, may relate to a programmable dual chamber pacemaker wherein the basic configuration of the pacemaker, e.g. unipolar or bipolar, can be changed, including the grounding configuration and ground potentials used within the pacemaker.

Generally, a heart stimulator, commonly known as a "pacemaker" or "pacer", uses one, two, or more flexible leads having one end connected to the pacer and the other end connected to electrodes placed in close proximity to the heart. These leads are used to stimulate or pace the heart. These leads are also used to sense the heart's electrical activity by sensing the heart's signals from their electrodes.

In order to properly pace or sense, the pacer has to be able to deliver a stimulating pulse to the heart or sense an electrical signal from the heart, and this requires that there be an electrical return path. If, within a given heart chamber, a unipolar lead is used—containing a single conductor—the return path is the conductive body tissue and fluids. The return path is connected to the pacer by connecting the pacer electrical common or ground to the pacer metal enclosure, typically referred to as the pacer case or housing. The case, in turn, makes contact with the body tissue and/or fluids. Then the current flows from the pacemaker through the lead's conductor, then through the lead's electrode, then through tissue, and finally to the pacer case.

An alternative solution to using a unipolar lead in a given heart chamber is to use a double lead/electrode in the heart chamber, known as a bipolar lead. In a typical bipolar lead, a second conductor coil or cable is spiraled over or positioned in a separate lumen and insulated from a first conductor along the length of the lead. At the distal end of the lead, one of the conductor cables or coils (inner) is connected to a first electrode, referred to as the "tip" electrode, and the second (outer) conductor coil is connected to a second electrode, referred to as a "ring" electrode. The ring electrode is generally situated about 10 to 20 mm from the tip electrode. The tip electrode is typically placed in contact with heart tissue, while the ring electrode is likely to be mostly in electrical contact with the blood. Because both body tissue and fluids are conductive, the ring electrode of a bipolar lead, in contact with the body fluids, serves as an electrical return for both pacing and sensing.

As indicated, pacing or sensing using the pacer case or enclosure as part of the electrical return path is known as unipolar pacing or sensing. Pacing or sensing using the lead ring electrode and an associated lead conductor as the electrical return path is known as bipolar pacing or sensing. There are numerous factors to consider when deciding whether unipolar or bipolar pacing and/or sensing should be used. Bipolar sensing is less prone to crosstalk, far field signals, and myopotential sensing than is unipolar sensing. Crosstalk generally refers to a pacer mistakenly sensing a heart activity in one heart chamber immediately after the other chamber is paced. Bipolar sensing reduces crosstalk resulting from a pacing stimulus in the opposite chamber. Bipolar pacing is also preferred as it minimizes the potential for pectoral or diaphragmatic stimulation.

Unipolar pacing and sensing offers the advantage, in general, of simpler circuitry within the pacemaker and a simpler, smaller diameter lead. In any event, cardiac pacing leads intended to be placed in the chambers of the heart, or nowadays, into the coronary venous system, are subjected to a series of tortuous bends that they must traverse. The leads must have the flexibility to follow these bends but have enough structural support to allow the leads to be pushed and twisted in order to navigate within these veins.

As earlier noted, the present invention has application to placing leads whose electrodes are either endocardial usage or epicardial usage. In the customary manner, a transvenous lead with an endocardial electrode provides an electrical pathway between the pacemaker, connected to the proximal end of the lead, and endocardial tissue in contact with the distal end of the lead. Endocardial tissue refers to a specific layer of tissue in the interior of the heart's chambers. In such a manner electrical pulses emitted by the pacemaker travel through the endocardial lead and stimulate the heart.

Transvenous leads with endocardial electrodes are often placed in contact with the endocardial tissue by passage through a venous access, such as the cephalic or subclavian veins or one of their tributaries. In such a manner transvenous leads offer as an advantage that their electrodes may be placed into contact with the heart without requiring major thoracic surgery. Rather, transvenous leads may be introduced into a vein and maneuvered therefrom so that their electrodes make contact with the endocardium of the heart.

A multi-step procedure is often used to introduce such leads within the venous system. Generally this procedure consists of inserting a hollow needle into a blood vessel, such as the subclavian vein. A wire guide is then passed through the needle into the interior portion of the vessel. The needle is then withdrawn and an introducer sheath and dilator assembly is then inserted over the wire guide into the vessel. The assembly is advanced into a suitable position within the vessel, i.e. so that the distal end is well within the vessel but the proximal end is outside the patient. Next, generally, the dilator and wire guide are both removed. It is also common to keep the wire guide in place, in case it is needed again. The introducer sheath is left in position and therefore offers direct access from outside the patient to the interior of the blood vessel. In such a fashion a transvenous lead can be easily passed into the vessel through the introducer sheath and ultimately be positioned within the heart. Finally the introducer sheath is removed from the body. With respect to pacemaker leads, however, which typically have a relatively bulky connector pin assembly at the proximal end, the introducer sheath is removed from the body by being split or slit apart. In such a manner the introducer sheath does not have to be large enough to be removed over the relatively bulky connector pin assembly at the proximal end of the lead.

An introducer sheath therefore, through its hollow lumen, provides access to the interior of a vessel. A transvenous lead introduced into the blood vessel may then moved along the blood vessel until properly positioned within the heart.

To provide such access an introducer sheath must be flexible. Specifically, flexibility permits the introducer sheath to bend and form to a curve compatible with the blood vessel. In such a manner the introducer sheath end is substantially parallel to the blood vessel and a lead which is introduced therethrough is properly oriented along the vessel interior. If the sheath did not conform to the vessel shape, a lead introduced would abut against the vessel wall, possibly injuring the patient and damaging the lead. One problem which may occur, however, due to the flexibility required of the introducer sheath is that the mid-portion of the sheath may form a kink.

Kinking within the introducer sheath may cause serious problems, especially with respect to pacemaker leads. Generally a kink within an introducer sheath is not detected until a lead is attempted to be introduced therethrough. At that time the lead, and in particular the delicate electrode at the distal end of the lead, strikes the kinked section and is blocked. Continual pushing on the lead may cause damage to the electrode as well as damage to the conductor and insulative sheath of the lead body. Because such damage may not be readily apparent, implantation of a damaged lead may result, in turn, creating the possibility of serious harm to the patient.

A further problem exists in pacemaker patients who have had multiple leads implanted over time. Scar tissue at the site of implantation has been found to create difficulties with past lead introduction systems. Specifically the relatively tough scar tissue hinders the introduction of a dilator and introducer sheath assembly. Many times, only through use of larger incisions than are otherwise desirable is such an assembly able to be inserted.

Others have proposed introducer systems that feature a sheath having a kink resistant section allowing the sheath to be bent in that region and still allow a lead to be introduced therethrough. The kink resistant section comprises a series of bellows or pleats. The bellows or pleats may be further arranged to form a screw about a portion of the sheath to thereby permit the sheath to be screwed into body tissue. The sheath preferably is constructed to readily split in a longitudinal direction and thus permits the system to be removed from the venous system without having to withdraw the sheath over an end of the pacemaker lead.

It was in light of the foregoing that the present invention was conceived and has now been reduced to practice.

SUMMARY

An introducer system for use with a pacemaker lead includes a plastic sheath compatible for insertion within a body, a first end configured for insertion into the body with a second end extending out of the body. A central lumen of the sheath is configured to permit introduction of the lead and includes a flexible, kink-resistant section smooth on its outer surface with a helical pleat defining a helical groove permitting the sheath to be screwed through tissue of the body and enabling a conductor extending from the mapping probe to the pacing system analyzer to be received in the helical groove of the sheath. A mapping probe at the first end of the sheath is connectable to a pacing system analyzer for seeking a location on the myocardial surface of the heart at which optimal pacing parameters can be achieved prior to implantation of the lead.

As earlier noted, the invention concerns an introducer which provides access for a lead to the interior of a vessel and into the heart or to the epicardial surface. To provide access to the desired implant site, the introducer must be able to bend and form a curve compatible with the anatomy of the patient. One problem that currently exists with conventional introducers is that the bending of the introducer may cause it to kink, this in turn occludes and thereby impedes access to the desired implant site. Furthermore, kinking can cause damage to the distal electrode of the lead by the continual pushing on the lead. An additional problem existing among current introducers is that they are not furbished with mapping capabilities. Mapping serves as a pre-screening for an implant site that offers the optimal pacing parameters.

In responding to the need to solve this problem, a mapping introducer is taught in this disclosure that will abet the implanter in "screening" for the best location on the endocardial or epicardial surface of the heart for optimal pacing parameters prior to implantation of the lead. More specifically, this invention disclosure teaches the use of convoluted PTFE (polytetrafluoroethylene), or other suitable plastic, tubing to be employed as an introducer. The helical convolutions allow for the introducer to be contorted through any tortuous pathway without kinking, thereby providing an occlusion-free passageway for a lead introduced through its lumen. The invention differs from the earlier mentioned closest-known prior art in that it teaches the use of an introducer with endocardial or epicardial mapping capabilities.

Helical features created along the convoluted surface provide grooves to accommodate at least one conductor that runs from the proximal to distal end of the introducer. Suitable connections can be made at each end for connections to a pacing system analyzer (PSA) and at least one mapping electrode respectively. The conductors lying on the outer surface of the introducer thereby eliminate the need for a separate lumen which in turn could make the introducer stiffer and therefore less maneuverable. The mapping probe electrode can be composed of a conductive polymer or a traditional material such as platinum or its alloys, stainless steel, or other suitable electrode materials for temporary electrical testing. The electrode could also be any of the above materials with a suitable material coating. The conductors employed in the introducer could include a coated cable or coated wire, wound into a coil.

A primary feature, then, of the present invention is the provision of an introducer system having a kink resistant sheath for the insertion of a pacemaker lead, the sheath having mapping capabilities for optimally positioning the lead at the endocardial or epicardial surface of the heart.

Another feature of the present invention is the provision of such an introducer system for which the outer surface of the sheath defines a helical groove for reception of at least one insulated conductor connecting a mapping probe electrode at a distal end to a pacing system analyzer.

Yet another feature of the present invention is the provision of such an introducer system which is appropriate for either myocardial or endocardial usage.

Still another feature of the present invention is the provision of such an introducer system which can be used with either a unipolar, bipolar, or multi-electrode leads.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

The present invention is not limited to use only in introducing atrial or ventricular cardiac pacing leads, and may be employed in introducing many of various types of therapeutic or diagnostic devices including transvenous leads intended to be disposed at various places within patient 10, including, for example, leads intended to be disposed within the patient's coronary sinus, as well as various other types of electrical leads, including nerve, muscle or defibrillation leads. It is to be further understood, moreover, the present invention may be employed in introducing many of various types of therapeutic or diagnostic catheters and is not limited only to the introduction of electrical leads. Also, the invention is concerned with the use of an introducer system intended to properly position a lead at the epicardial surface of the heart.

For purposes of illustration only, however, the present invention is below described in the context of the introduction of transvenous pacing leads with endocardial electrodes, of either the passive fixation or of the active fixation configuration.

Figure 1:
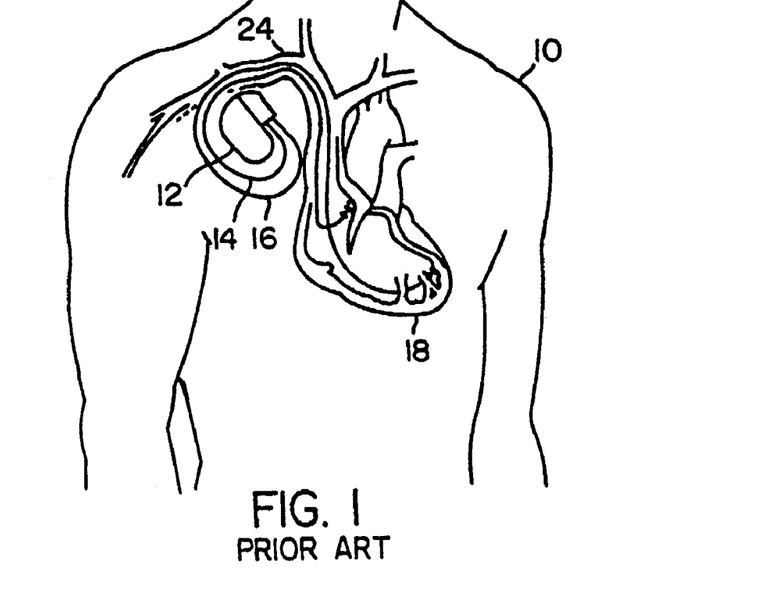
FIG. 1 is a perspective view of a patient's chest depicting the venous positioning and placement of transvenous endocardial leads in the patient.

FIG. 1 depicts a typical arrangement of a pacing system implanted in a patient 10, the pacing system employing a subcutaneously disposed pacemaker 12 and transvenous pacing leads 14 and 16. In FIG. 1, the distal end of pacing lead 14 is shown disposed generally in the atrial region of the patient's heart 18, while the distal end of pacing lead 16 is disposed generally in the ventricular region of the heart.

A preferred prior art method of lead introduction compatible with an introducer system in accordance with the present invention will be described with reference to FIGS. 2 through 17.

Figure 2:
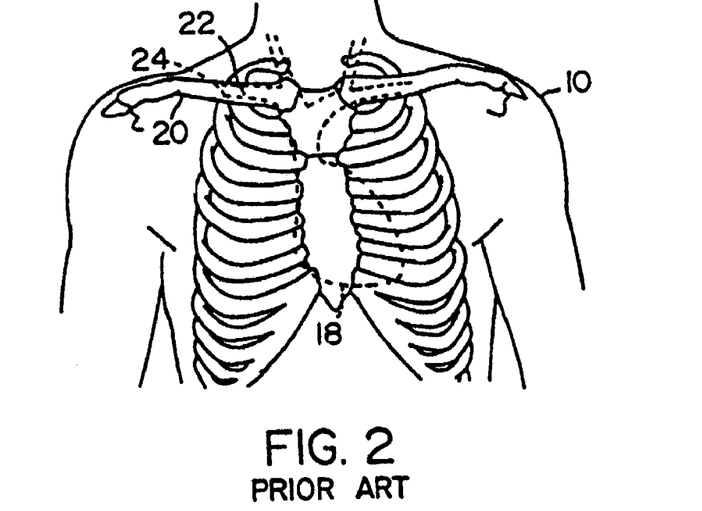
FIG. 2 is a front elevation of the patient's chest depicting an appropriate entry site for implantation of a transvenous endocardial lead.

Referring to FIG. 2, and in accordance with common practice in the medical arts, the entry site for a subclavian vein puncture is commonly chosen to be just below and slightly medial to the junction of the middle and inner third of the clavicle 20, at an area designated generally as 22 in FIG. 2. In FIG. 2, the patient's subclavian vein 24 and heart 18 are shown in phantom.

Figure 3:
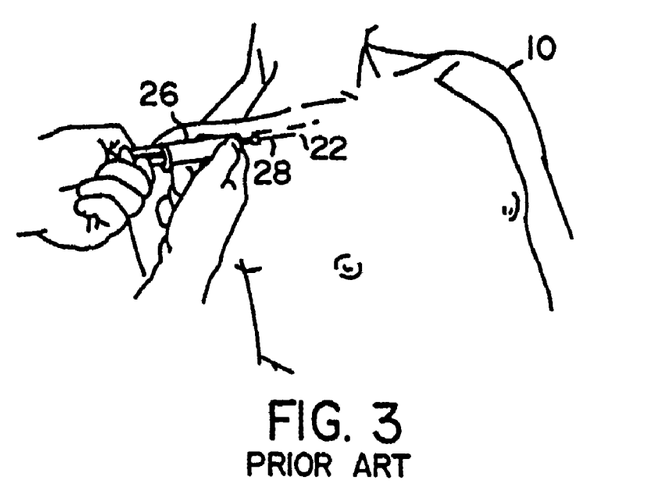
FIG. 3 is a perspective view of a patient's chest depicting an initial stage of introducing a transvenous endocardial lead into a vein.
Figure 4:
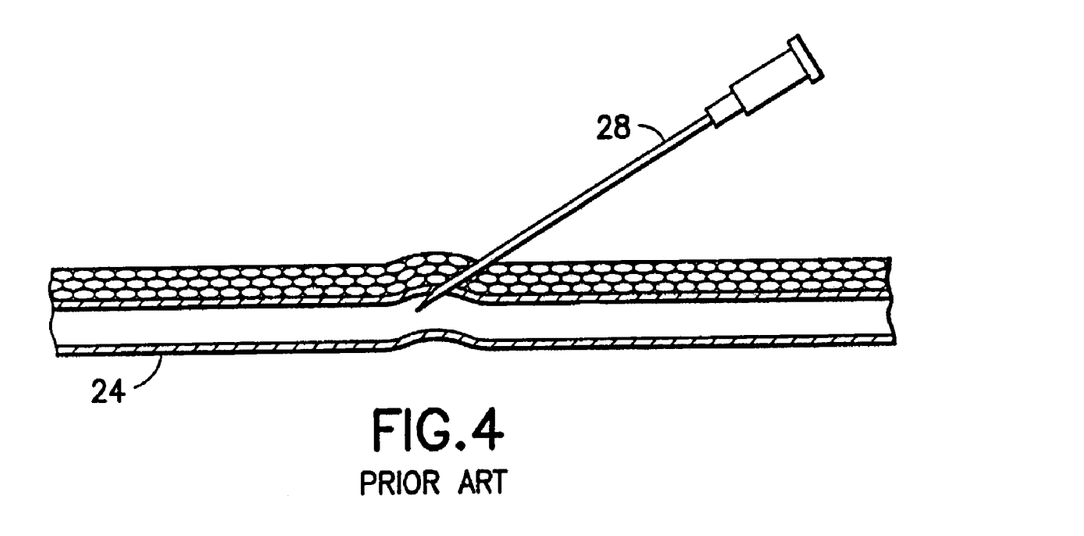
FIG. 4 is a longitudinal cross section view of a vein depicting the initial stage of introducing the transvenous endocardial lead as illustrated in FIG. 3.

Turning to FIG. 3, the subclavian vein puncture is accomplished by the physician using a disposable syringe 26 having a detachably connected thin-wall needle 28. Aspiration is performed as the needle is advanced into the subclavian vein, to verify proper needle placement within vessel 24. Next, aspirating syringe 26 is disconnected from needle 28 which remains in vessel 24, as shown in FIG. 4. Typically, the physician will place a finger over the needle to avoid air aspiration and excessive bleeding.

Figure 5:
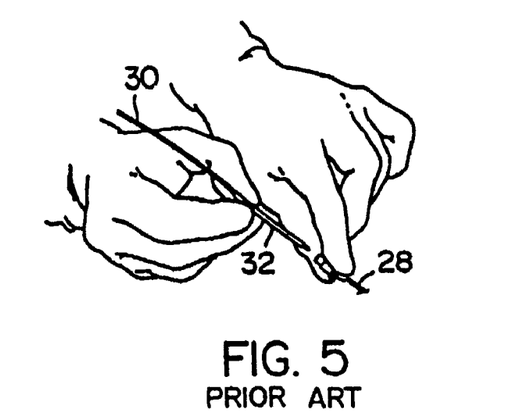
FIG. 5 is a perspective view depicting a subsequent stage of introducing the transvenous endocardial lead.
Figures 6, 7:
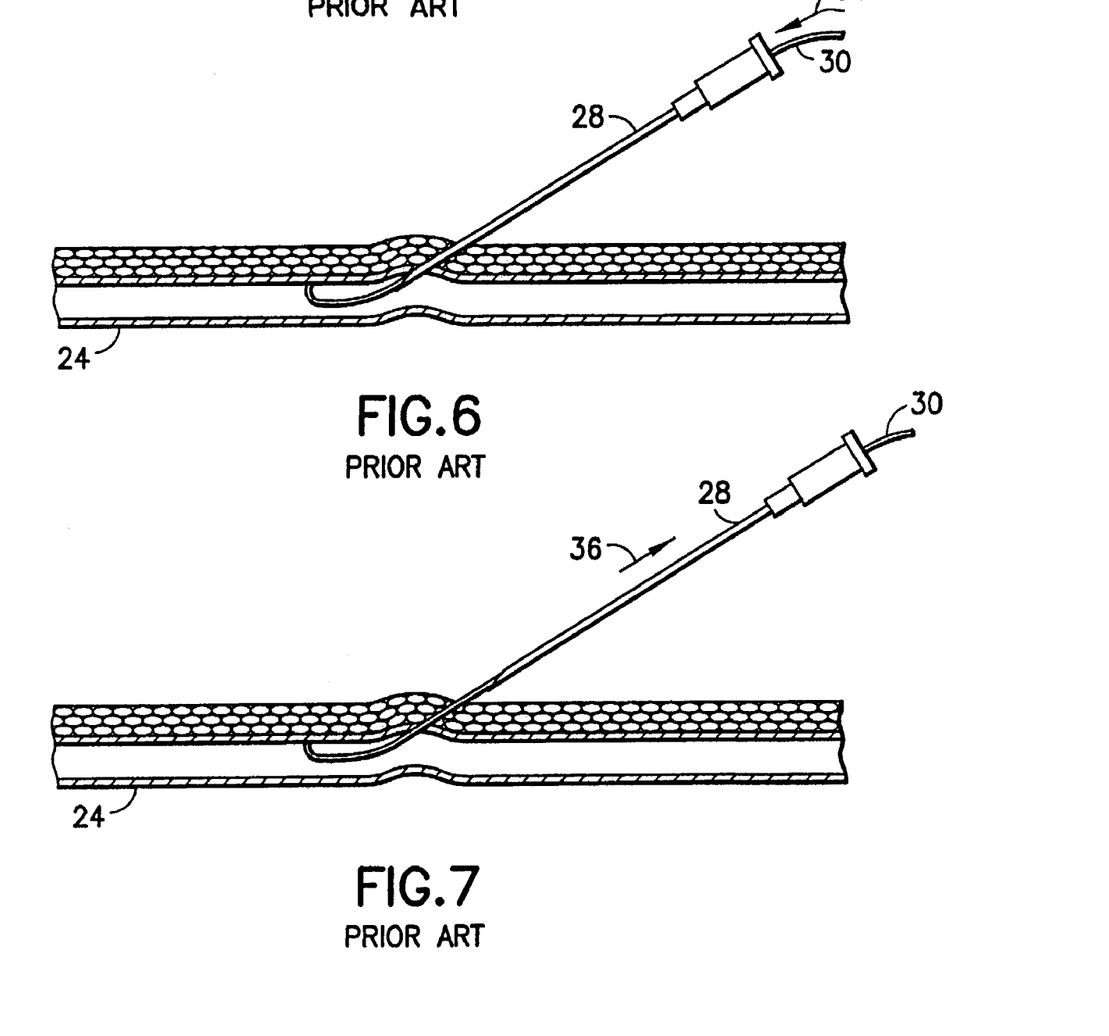
FIGS. 6–14 are further views that depict further successive stages of introducing a transvenous endocardial lead into a vein.

The next step in the lead implantation procedure involves insertion of a conventional J-type guide wire 30 through needle 28, as illustrated in FIG. 5. Typically, guide wire 30 is equipped with a tip deflector 32 for facilitating insertion of wire 30 into the lumen of needle 28. As shown in FIG. 6, as wire 30 is fed through needle 28 in the direction of arrow 34, the distal end of wire 30 exits the tip of needle 28, and wire 30 regains its "J" shape within vessel 24. Once wire 30 has entered vessel 24, needle 28 is withdrawn in the direction of arrow 36 in FIG. 7, leaving wire 30 in place. Wire 30 is advanced along vessel 24 until its distal end is disposed generally in the area of the patient's superior vena cava, leaving approximately 15 to 20-cm of the proximal end of wire 30 exposed.

Figure 8:
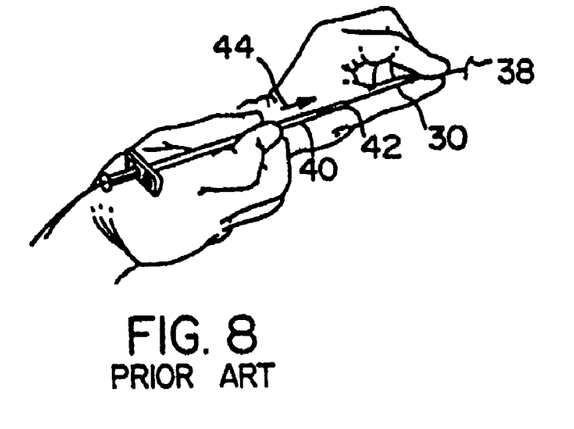
Figure 9:
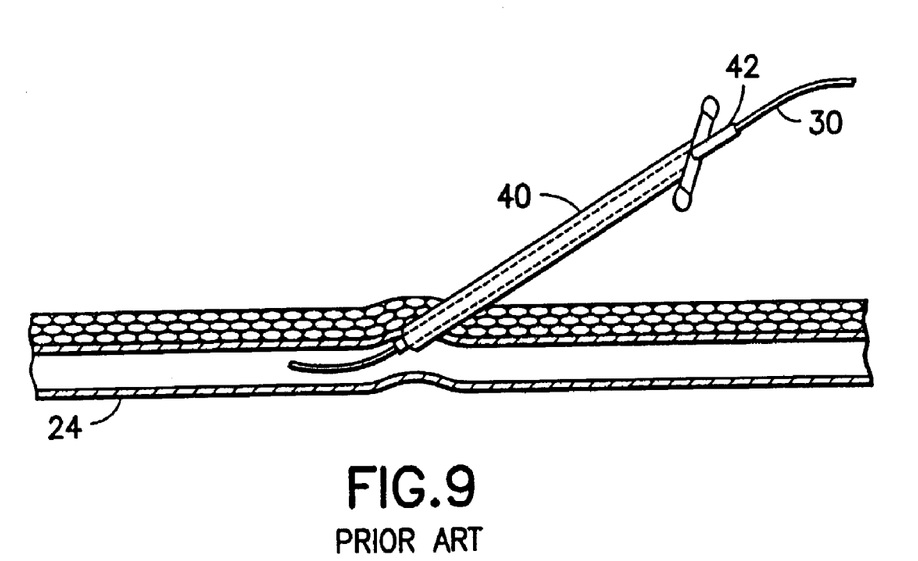

A small skin incision 38 is made at the guide wire entry site, parallel to clavicle 20. This will later become the "pacemaker pocket". In the next stage of the implantation procedure, as shown in FIG. 8, an introducer sheath 40 with tapered vessel dilator 42, as an assembly, are threaded onto the proximal end of wire 30. Sheath 40 and dilator 42 are advanced in the direction of arrow 44, through the subclavian fascia and into subclavian vein 24, until a short length (e.g., 2 to 8-cm) of sheath 40 and vessel dilator 42 remain exposed along with the wire guide, as shown in FIG. 9.

Figure 10:
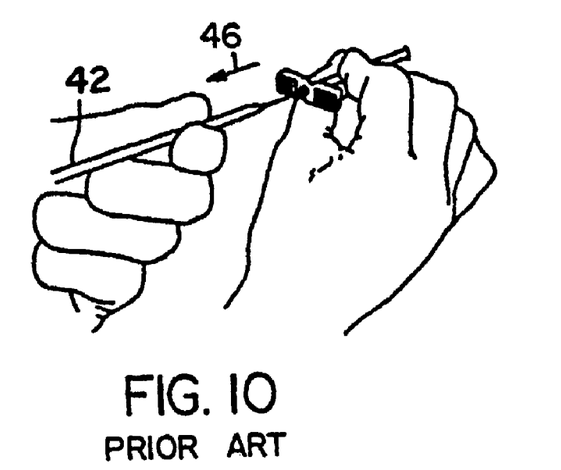
Figure 11:
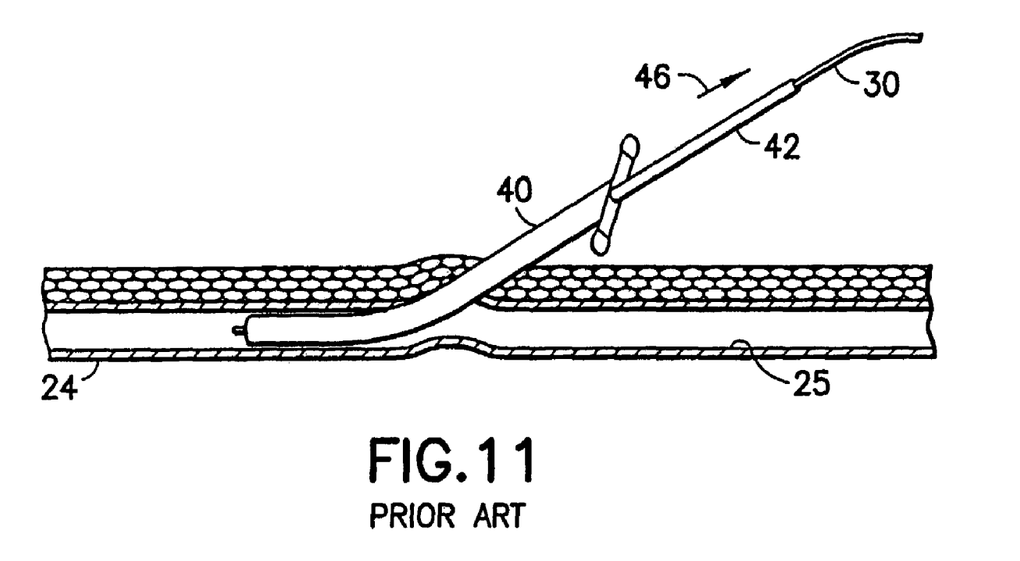

Next, as shown in FIGS. 10 and 11, vessel dilator 42 is withdrawn in the direction of arrow 46 and sheath 40 is introduced further within subclavian vein 24, leaving introducer sheath 40 and guide wire 30 in place with its 40 distal end disposed within subclavian vein 24. Guide wire 30 may be removed at this point as well, although it may be left in place in case the lead needs to be repositioned or reinserted or an additional lead needs to be inserted. As shown in FIG. 11, introducer sheath 40 must bend to conform to the shape of subclavian vein 24 to provide an unobstructed conduit for lead 14 to be introduced. Through such curvature, moreover, lead 14 may be introduced so as to be parallel to vein 24 and not abut and damage wall 25 of subclavian vein 24.

Figure 12:
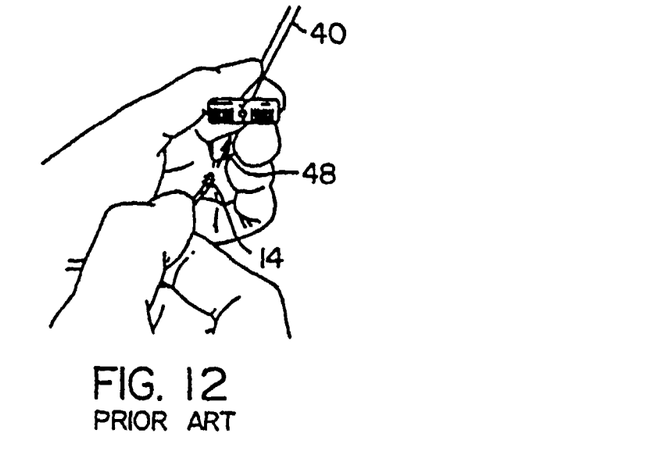
Figure 13:
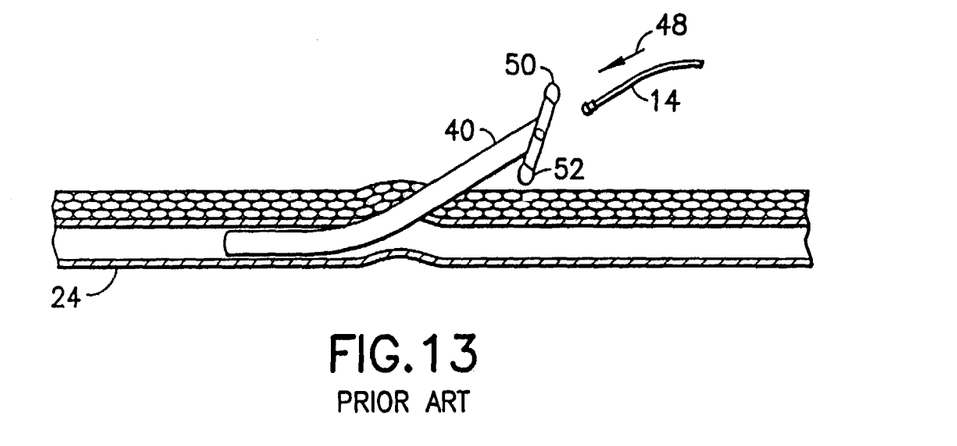
Figure 14:
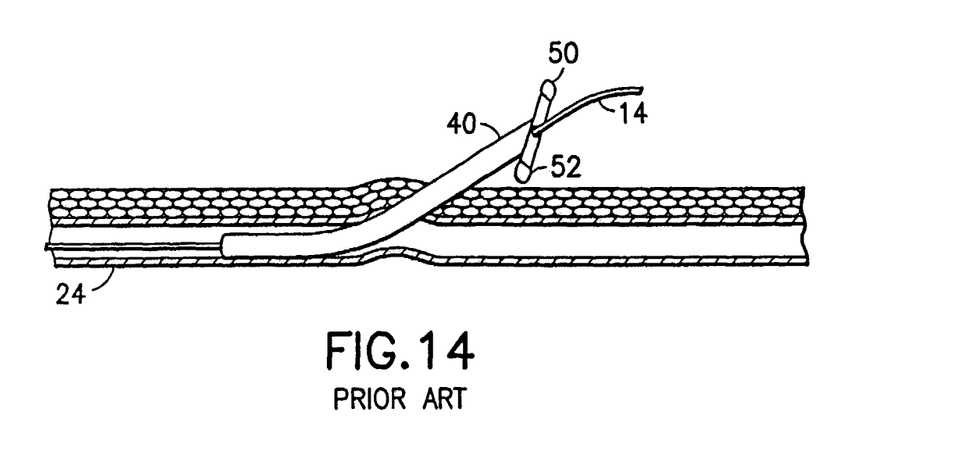

In the final stages of the lead implantation procedure, illustrated in FIGS. 12 through 14, pacing lead 14 is inserted into the proximal end of introducer sheath 40 in the direction of arrow 48, and advanced into the desired position within patient 10 through vessel 24. Lastly, introducer sheath 40 is removed. Removal of introducer sheath 40 may be accomplished in one of several known ways, depending upon the particular type of introducer sheath 40. For example, as disclosed in U.S. Pat. No. 4,306,562 to Osborne, sheath 40 may be longitudinally split by pulling tabs 50 and 52. Other sheaths are known which are severable by means of a special slitter device or the like.

As shown in FIG. 1, pacemaker 12 may operate in conjunction with two pacing leads. In that case, as with single-lead implants, it may be necessary to keep guide wire 30 in place until after the first lead has been implanted. Thus, as previously noted with reference to FIGS. 10 and 11, guide wire 30 may be left in place when dilator 42 is withdrawn. The first lead, if it is sufficiently small, may be introduced into subclavian vein 24 alongside guide wire 30, and then the first introducer sheath is removed leaving guide wire 30 in place. Then, a second introducer sheath and vessel dilator can be guided along guide wire 30 in the same manner as the first, before guide wire 30 is finally removed.

Figure 15:
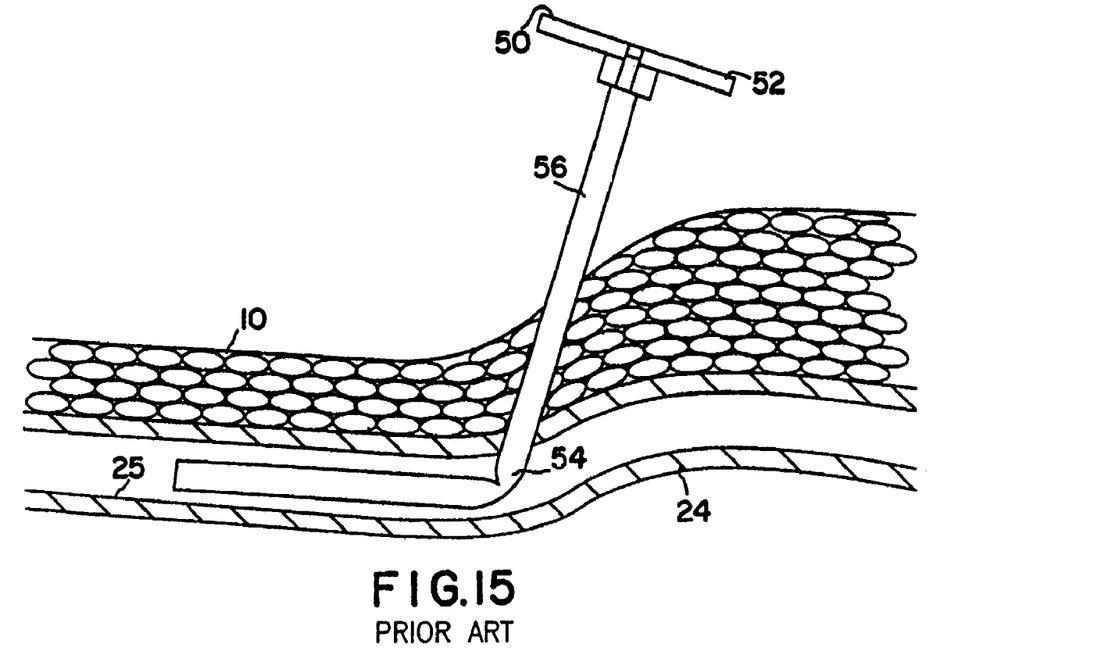
FIG. 15 is a longitudinal cross section view of a vein depicting a known introducer sheath used in a body and subjected to a kink.

As depicted in FIG. 15 one problem associated with lead introduction systems and particularly with the sheath used in previous lead introduction systems is the formation of a kink 54. As seen, a kink 54 in sheath 56 prevents lead 14 from being introduced therethrough. As mentioned, such kinks may be undetected so that a lead inserted into the sheath is blocked or impeded, possibly resulting in damage to the lead.

Figures 16, 18C:
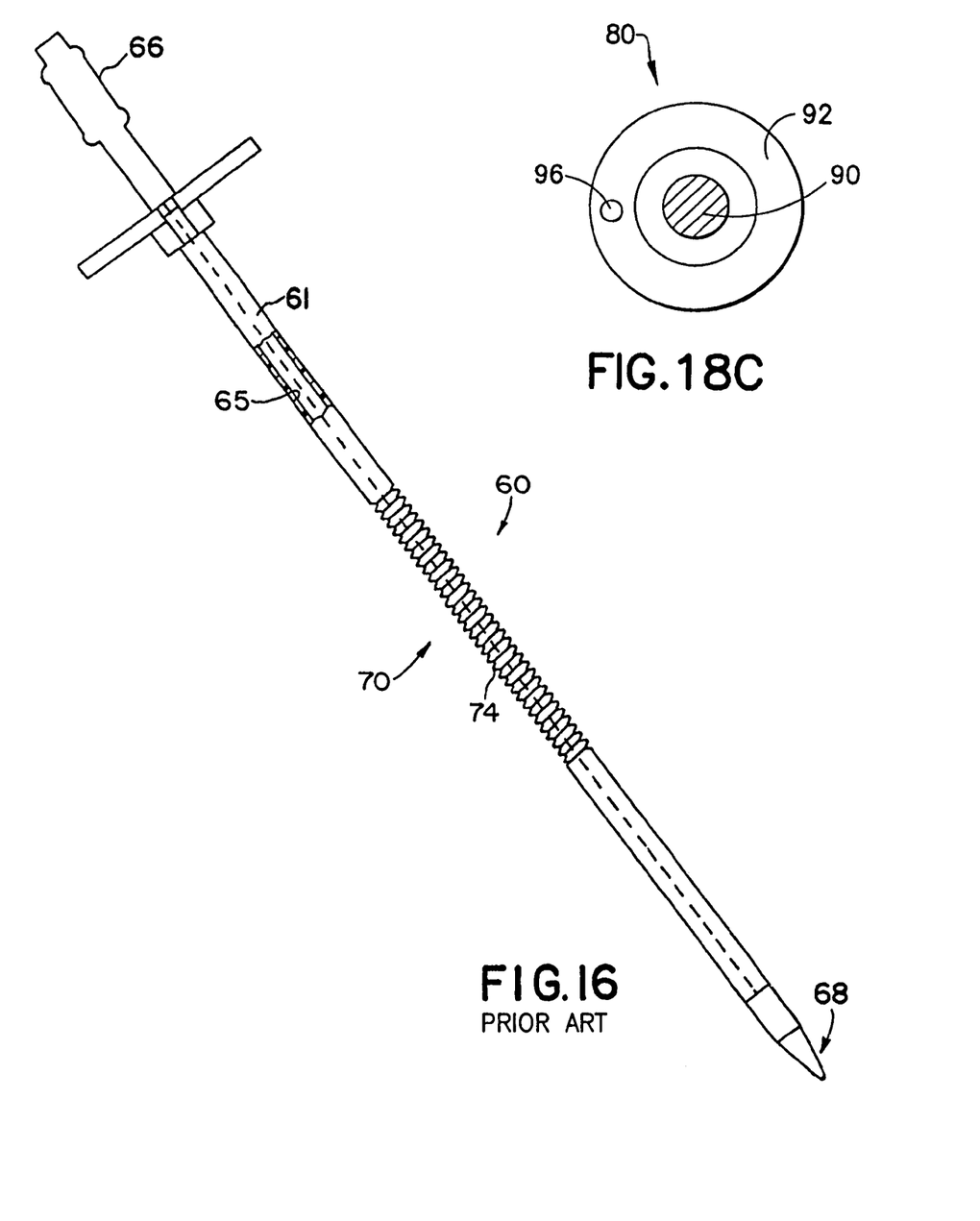
FIG. 16 is an elevation view depicting a known lead introducer system.
FIG. 18C is a distal end elevation view of a modification of the lead introducer system illustrated in FIG. 18.

Turning now to FIG. 16, a known introducer system 60 is illustrated which is of a type disclosed in earlier mentioned U.S. Pat. No. 5,409,469. The introducer system 60 comprises an introducer sheath 61 preferably made from a biocompatible plastic, such as polytetrafluoroethylene into which a vessel dilator 66 is inserted. Tapered end 68 of vessel dilator 66 facilitates the introduction of sheath 61 into the subclavian vessel 24. Thereafter, guide wire 30 and vessel dilator 66 are withdrawn from the patient and central lumen 65 within sheath 61 provides access to the vessel 24.

Figure 17:
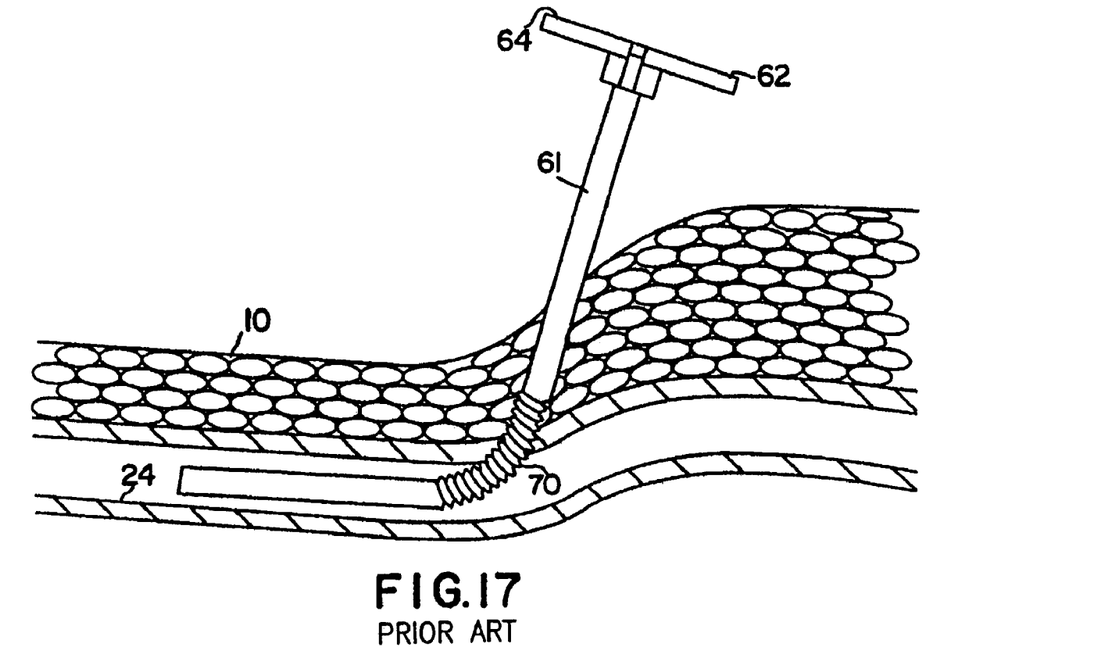
FIG. 17 is a longitudinal cross section view of a vein depicting the known introducer sheath of FIG. 16 used in a body and not subjected to a kink.

As seen in FIG. 16, the introducer sheath 61 has a kink resistant section 70 with a helical pleat 74 forming a screw configuration on its outer surface, thereby enabling the sheath to bend more readily within a body 10 without the formation of kinks as best seen in FIG. 17.

Figure 18:
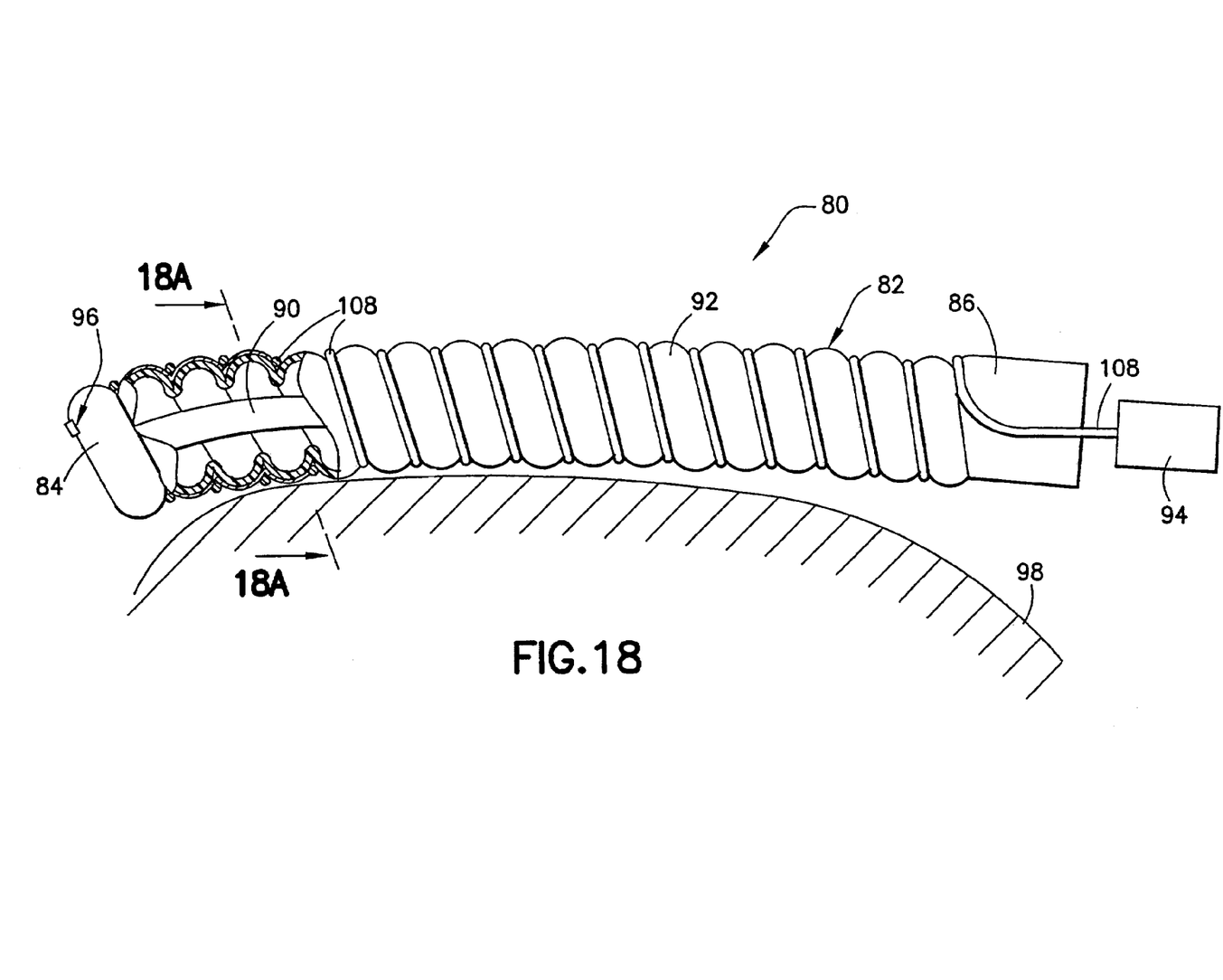
FIG. 18 is an elevation view depicting one embodiment of a lead introducer system of the present invention.
Figure 18A:
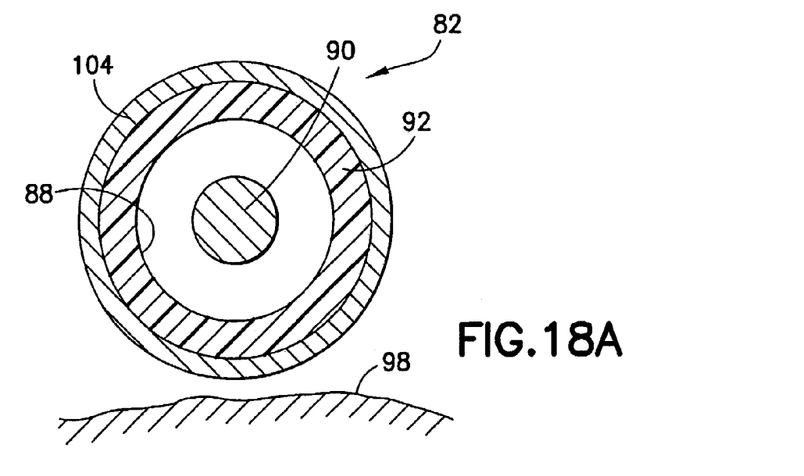
FIG. 18A is a cross section view taken generally along line 18A—18A in FIG. 18.
Figure 18B:
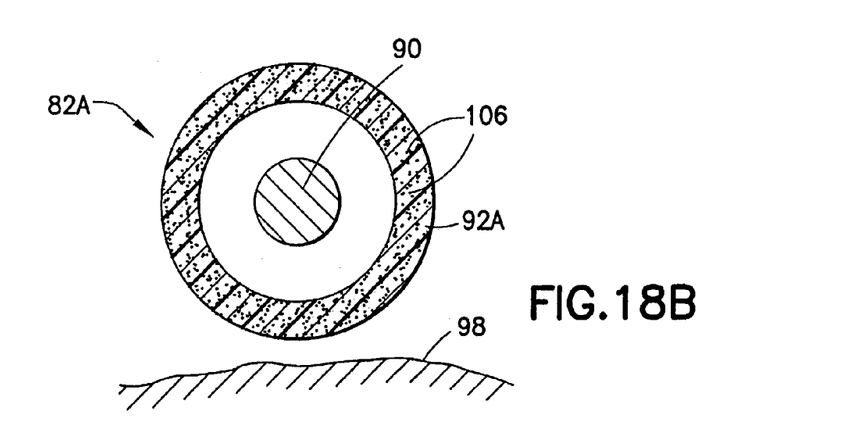
FIG. 18B is a cross section view, similar to FIG. 18A illustrating another embodiment of the invention.
Figure 19:
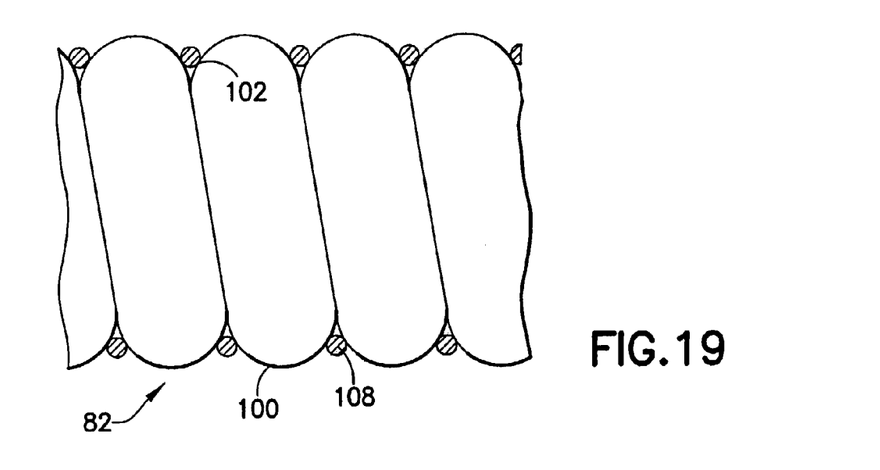
FIG. 19 is a detail elevation view of a portion of the lead introducer system of the invention.

For a description of the unique construction of an introducer system 80 utilizing the introducer sheath 82 of the invention, turn now, initially, to FIGS. 18, 18A, 18B, and 19. Although the present invention will be described with reference to the embodiments shown in the drawings, it should be understood that the present invention can be embodied in many alternate forms or embodiments. In addition, any suitable size, shape or type of elements or materials consistent with the invention could be used. The introducer sheath 82 which is composed of PTFE or other suitable plastic material extends between first and second ends, 84, 86, respectively, and is compatible for insertion within a body. As earlier described, the first end 84 is suitably configured for insertion of the sheath 82 within the body with the second end 86 extending out of the body. As seen in FIG. 18A, the sheath 82 has a central lumen 88 configured to permit the through introduction of at least one lead 90 (FIG. 18A) or catheter. A flexible, kink-resistant section 92 is located along the sheath 82 and, indeed, is illustrated in FIG. 18 as extending almost the entire length of the sheath. A pacing system analyzer 94 for measuring characteristics of the heart is an important component of the introducer system 80 and is connected to the introducer sheath 82 in a manner to be explained. A mapping probe 96 at the first end 84 of the sheath 82 is connectable to the pacing system analyzer for the purpose of seeking an epicardial surface location 98 or an endocardial location, not illustrated in this instance, but generally as illustrated in FIGS. 9, 11, 13, and 14 with the description relating to those figures, at which optimal pacing parameters can be determined prior to implantation of the lead 90 or catheter.

The flexible, kink-resistant section 92 is smooth on its outer surface permitting the sheath to slide smoothly through tissue of the body and is formed in the nature of a helical pleat 100 (FIG. 19) on the its outer surface defining a helical groove 102. The mapping probe 96 is a distal tip electrode. In one instance, especially viewing FIG. 18A, a discrete length of the outer surface of the sheath 82 may have a coating 104 of a metal such as platinum or a platinum alloy to produce the mapping probe. In another instance (FIG. 18B), the electrode may be composed of a conductive polymer, that is, particles 106 of a metal such as platinum or a platinum alloy may be embedded in the plastic material of a modified introducer sheath 82A to produce the mapping probe 96. A flexible, kink-resistant section 92A is located along the sheath 82A. In either instance, a conductor 108 is received in the helical groove 102 of the sheath 82 and is suitably connected to, and extends from, the mapping probe 96 to the pacing system analyzer 94.

Figure 20:
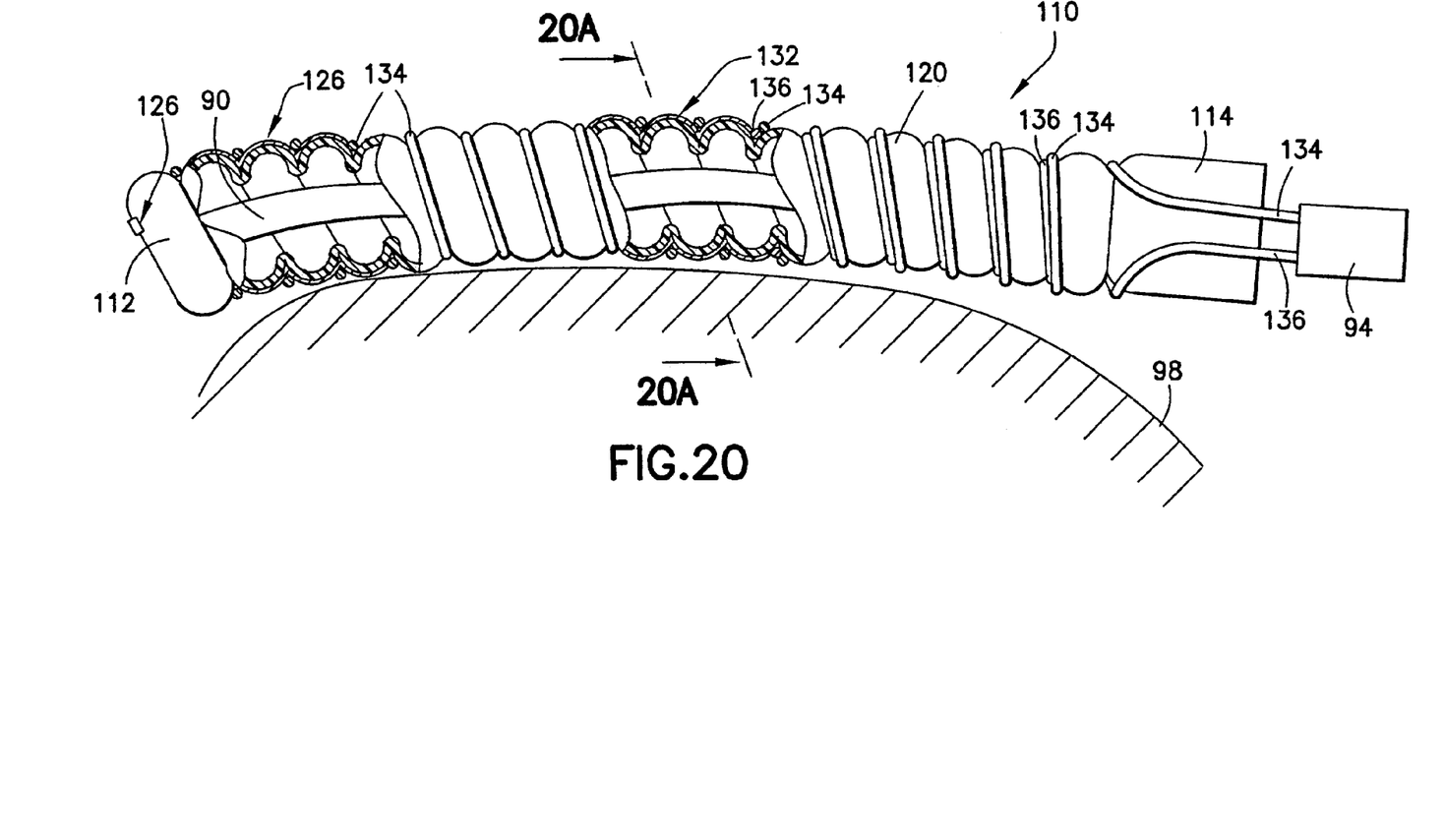
FIG. 20 is an elevation view of another embodiment of the lead introducer system of the invention, certain parts being cut away and shown in section.
Figure 20A:
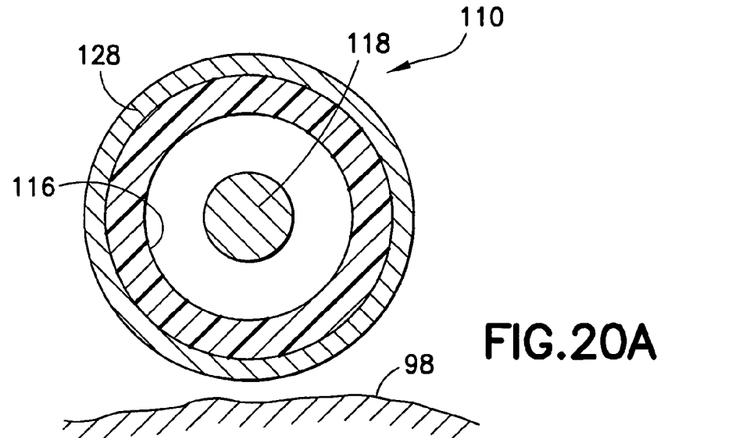
FIG. 20A is a cross section view taken generally along line 20A—20A in FIG. 20.
Figure 20B:
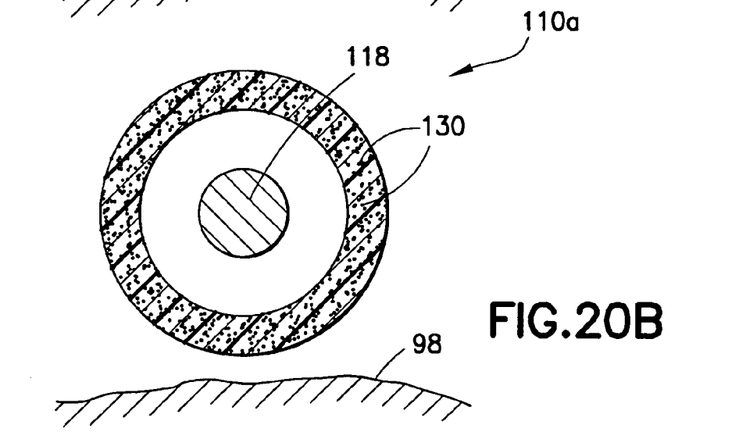
FIG. 20B is a cross section view, similar to FIG. 20A illustrating another embodiment of the invention.
Figure 21:
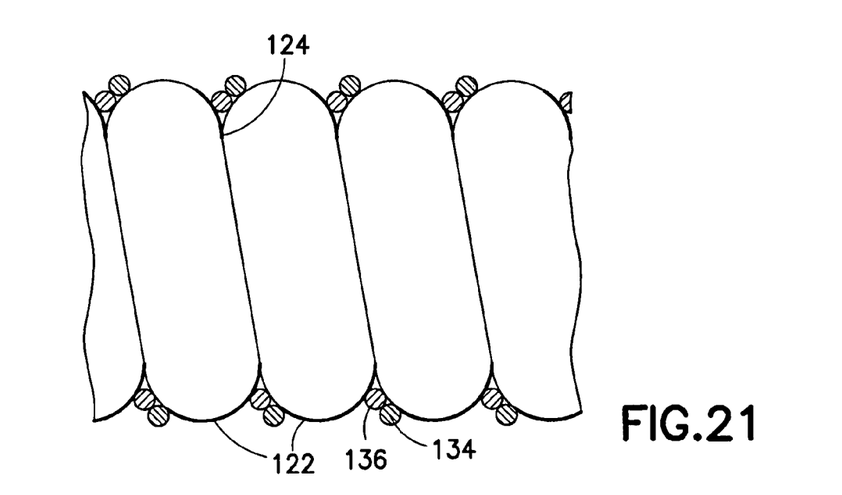
FIG. 21 is a detail elevation view, similar to FIG. 19, of a portion of another embodiment of the lead introducer system of the invention.

Turn now to FIGS. 20, 20A, 20B, and 21 for the description of another embodiment of the introducer system 80, this time utilizing an introducer sheath 110. The introducer sheath 110, which is also composed of PTFE or other suitable plastic material, extends between first and second ends, 112, 114, respectively, and is compatible for insertion within a body. Also as earlier described, the first end 112 is suitably configured for insertion of the sheath 110 within the body with the second end 114 extending out of the body. As seen in FIG. 20A, the sheath 110 has a central lumen 116 configured to permit the through introduction of at least one lead 118 or catheter. A flexible, kink-resistant section 120 is located along the sheath 110 and, indeed, is illustrated in FIG. 20 as extending almost the entire length of the sheath. The pacing system analyzer 94, described with respect to the preceding embodiment, for measuring characteristics of the heart, is again an important component of the introducer system utilizing the introducer sheath 110 and is connected to the introducer sheath 110 in a similar manner.

As in the earlier described embodiment, the flexible, kink-resistant section 120 is smooth on its outer surface permitting the sheath to slide smoothly through tissue of the body and is formed in the nature of a helical pleat 122 (FIG. 21) on the its outer surface defining a helical groove 124. The mapping probe electrode includes a cathodal tip electrode 126. In one instance, especially viewing FIG. 20A, a discrete length of the outer surface of the sheath 110 may have a coating 128 of a metal such as platinum or a platinum alloy to produce the mapping probe. In another instance, viewing FIG. 20B, the electrode may be composed of a conductive polymer, that is, particles 130 of a metal such as platinum or a platinum alloy or other suitable electrode materials for temporary electrical testing may be embedded in the plastic material adjacent to, or at, the distal end of the modified introducer sheath 110A to produce the mapping probe.

An anodal ring electrode 132 is spaced from the cathodal tip electrode 126 and encircles the outer surface of the sheath 110 and is constructed in a manner similar to the cathodal tip electrode 126. First and second insulated conductors 134, 136 are received in the helical groove 124 of the sheath 110 suitably connected to and extending, respectively, from the cathodal tip electrode 126 and from the anodal ring electrode 132 to the pacing system analyzer 94. In another instance as seen in FIG. 20 (not shown), the anode may be located near the distal tip as a point or ring electrode.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An introducer system for use with at least one of a catheter and a lead, the introducer system comprising:
a sheath having a first end and a second end, the sheath being compatible for insertion within a body, wherein the sheath defines a central lumen configured to permit introduction of at least one of a lead and a catheter therethrough;
wherein at least a portion of the sheath is configured to define a flexible, kink-resistant section;
wherein the flexible, kink-resistant section comprises a helical pleat on an outer surface of the sheath defining a helical groove;
a mapping probe at the first end of the sheath connectable to a pacing system analyzer for seeking at least one of an epicardial surface location and an endocardial location at which optimal pacing parameters can be determined; and
at least one conductor received in the helical groove of the sheath connected to and extending from the mapping probe to the pacing system analyzer.

2. The introducer system of claim 1:
wherein the flexible, kink-resistant section is smooth on its outer surface permitting the sheath to be slid through tissue of the body.

3. The introducer system of claim 1:
wherein the sheath is formed of plastic.

4. The introducer system of claim 3:
wherein the plastic is composed of at least one of PTFE, PEBAX, polyurethane, polypropylene, and polyethylene.

5. The introducer system of claim 1:
wherein each conductor is a coated cable conductor; and
wherein the coating on the conductor is at least one of PTFE and ETFE.

6. The introducer system of claim 1:
wherein the mapping probe comprises a cathodal tip electrode; and further comprising:
an anodal ring electrode spaced from the cathodal tip electrode and encircling the outer surface of the sheath.

7. An introducer system for use with at least one of a catheter and a lead, the introducer system comprising:
a sheath having a first end and a second end, the sheath being compatible for insertion within a body, wherein the sheath defines a central lumen configured to permit introduction of at least one of a lead and a catheter therethrough;
wherein at least a portion of the sheath is configured to define a flexible, kink-resistant section;
a mapping probe at the first end of the sheath connectable to a pacing system analyzer for seeking at least one of an epicardial surface location and an endocardial location at which optimal pacing parameters can be determined;
wherein the mapping probe is a cathodal tip electrode; and further comprising:
an anodal ring electrode spaced from the cathodal tip electrode and encircling the outer surface of the sheath; and
first and second insulated conductors received in a helical groove of the sheath connected to and extending, respectively, from the cathodal tip electrode and from the anodal ring electrode to the pacing system analyzer.

8. The introducer system of claim 7:
wherein the cathodal tip electrode and the anodal ring electrode are composed of at least one of a conductive polymer, platinum, a platinum alloy, stainless steel, and another metal alloy.

9. An introducer system for use with at least one of a catheter and a lead, the introducer system comprising:
a sheath having a first end and a second end, the sheath being compatible for insertion within a body, the sheath having a central lumen configured to permit introduction of at least one of a lead and a catheter therethrough;
wherein at least a portion of the sheath is configured to define a flexible, kink-resistant section;
wherein the flexible, kink-resistant section comprises a helical pleat on an outer surface of the sheath defining a helical groove;
a pacing system analyzer that is operative to measure characteristics of a heart;

a mapping probe at the first end of the sheath that is connectable to the pacing system analyzer; and at least one conductor received in the helical groove of the sheath connected to and extending from the mapping probe to the pacing system analyzer.

10. The introducer system of claim 9:

wherein the flexible, kink-resistant section is smooth on its outer surface permitting the sheath to be slid through tissue of the body.

11. The introducer system of claim 9:

wherein the sheath is formed of plastic.

12. The introducer system of claim 11:

wherein the sheath is composed of at least one of PTFE, PEBAX, polyuretuane, polypropylene, and polyethylene.

13. The introducer system of claim 9:

wherein the mapping probe comprises a distal tip electrode.

14. The introducer system of claim 9:

wherein the mapping probe is a cathodal tip electrode; and further comprising:

an anodal ring electrode spaced from the cathodal tip electrode and encircling an outer surface of the sheath.

15. The introducer system of claim 14:

wherein the cathodal tip electrode and the anodal ring electrode are composed of at least one of a conductive polymer, platinum, a platinum alloy, stainless steel and another metal alloy.

* * * * *